United States Patent
Andriasyan

(10) Patent No.: US 7,288,086 B1
(45) Date of Patent: *Oct. 30, 2007

(54) HIGH-EFFICIENCY, SIDE-PUMPED DIODE LASER SYSTEM

(75) Inventor: Manvel Artyom Andriasyan, San Diego, CA (US)

(73) Assignee: Biolase Technology, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/178,080

(22) Filed: Jun. 21, 2002

Related U.S. Application Data

(60) Provisional application No. 60/299,944, filed on Jun. 21, 2001.

(51) Int. Cl.
*A61B 18/20* (2006.01)

(52) U.S. Cl. .................... 606/14; 128/898; 433/29; 606/2

(58) Field of Classification Search ............ 606/10–18; 372/69–75; 433/29
See application file for complete search history.

(56) References Cited

U.S. PATENT DOCUMENTS

| | | | | |
|---|---|---|---|---|
| 5,181,223 A * | 1/1993 | Baer et al. | ..................... | 372/69 |
| 5,192,279 A * | 3/1993 | Samuels et al. | ............... | 606/17 |
| 5,200,966 A * | 4/1993 | Esterowitz et al. | ............ | 372/71 |
| 5,363,387 A * | 11/1994 | Sinofsky | ..................... | 372/15 |
| 5,401,171 A * | 3/1995 | Paghdiwala | .................. | 606/13 |
| 5,415,652 A * | 5/1995 | Mueller et al. | ................. | 606/3 |
| 5,423,798 A * | 6/1995 | Crow | ............................. | 606/4 |
| 5,458,594 A * | 10/1995 | Mueller et al. | ................. | 606/3 |
| 5,554,029 A * | 9/1996 | Kowalyk et al. | ............ | 433/215 |
| 5,623,510 A * | 4/1997 | Hamilton et al. | .............. | 372/75 |
| 5,940,425 A * | 8/1999 | Lasser et al. | .................. | 372/72 |
| 6,050,991 A * | 4/2000 | Guillet | ........................ | 606/10 |
| 6,086,366 A * | 7/2000 | Mueller et al. | ................ | 606/12 |
| 6,090,102 A * | 7/2000 | Telfair et al. | .................. | 606/10 |
| 6,179,830 B1 * | 1/2001 | Kokubu | ........................ | 606/16 |
| 6,213,998 B1 * | 4/2001 | Shen et al. | ..................... | 606/10 |
| 6,235,017 B1 * | 5/2001 | Jegorov et al. | ................. | 606/16 |
| 6,288,499 B1 * | 9/2001 | Rizoiu et al. | ............ | 315/200 A |
| 6,458,120 B1 * | 10/2002 | Shen et al. | .................... | 606/10 |
| 6,607,524 B1 * | 8/2003 | LaBudde et al. | ............. | 606/10 |
| 6,631,153 B2 * | 10/2003 | Sumiyoshi et al. | ........... | 372/75 |

OTHER PUBLICATIONS

Observation of enhanced thermal lensing due to near-Gaussian pump energy deposition in a laser-diode side-pumped Nd:YAG laser;David Welford, David M. Rines, Bradley J. Dinerman, and Robert Martinsen;IEEE Journal of Quantum Electronics, vol. 28, No. 4, 1992.*

(Continued)

*Primary Examiner*—Henry M Johnson, III
(74) *Attorney, Agent, or Firm*—Stout, Uxa, Buyan & Mullins, LLP

(57) ABSTRACT

An apparatus for cutting or ablating hard tissue, includes an optical cavity; a gain medium disposed within the optical cavity; a diode light pump disposed within the optical cavity and optically aligned to light pump the gain medium to generate laser light. The generated laser light has a wavelength and power density suitable for cutting and ablating hard tissue.

38 Claims, 7 Drawing Sheets

OTHER PUBLICATIONS

High power 1.9 micron pumped solid-state holmium lasers, Budni et al; Lasers and Electro-Optics, 2000. (CLEO 2000). Conference on , May 7-12, 2000 p. 564.*

CW Laser Operation From Er:YAG, Er:GGG, Er:YSGG And Er:BYF, Dinerman, B.J. et al; Lasers and Electro-Optics Society Annual Meeting, 1992. LEOS '92, Conference Proceedings , Nov. 16-19, 1992, pp. 310-311.*

1.8-W CW Er:YLF diode-pumped laser, Dergachev, A.Y.; Flint, J.H.; Moulton, P.F.; Lasers and Electro-Optics, 2000. (CLEO 2000). Conference on , May 7-12, 2000, pp. 564-565.*

* cited by examiner

HIGH-EFFICIENCY, SIDE-PUMPED DIODE LASER SYSTEM

CROSS-REFERENCE TO RELATED APPLICATIONS

This application claims the benefit of U.S. Provisional application No. 60/299,944, filed Jun. 21, 2001 and entitled HIGH-EFFICIENCY, SIDE-PUMPED DIODE LASER SYSTEM.

BACKGROUND OF THE INVENTION

1. Field of the Invention

The present invention relates generally to cutting devices and, more particularly, to diode laser systems.

2. Description of Related Art

Prior art laser diode pumped lasers have been either end-pumped as demonstrated in FIG. 1a or side-pumped. End pumping configurations can be more efficient and can produce a better transverse mode. In FIG. 1a, wherein "HR" denotes a high reflectivity element and "OC" denotes an output coupling element, laser output is focused into a fiber via a lens. Side pumping constructions, on the other hand, can be more scalable therefore enabling the generation of relatively high laser power and energy.

SUMMARY OF THE INVENTION

In accordance with one aspect of the present invention, a method of cutting or ablating hard tissue is disclosed, comprising the steps of providing a gain medium, a diode array, and an optical cavity; placing the gain medium and the diode array within the optical cavity so that the diode array is optically aligned to side pump the gain medium; activating the diode array to light pump the gain medium and generate laser light; and directing the laser light onto the hard tissue to cut or ablate the hard tissue.

In accordance with another aspect of the present invention, a method of cutting or ablating hard tissue, comprises the steps of providing a gain medium, a diode light pump, and an optical cavity; placing the gain medium and the diode light pump within the optical cavity so that the diode light pump is optically aligned to light pump the gain medium; activating the diode light pump to light pump the gain medium and generate laser light; and directing the laser light onto the hard tissue to cut or ablate the hard tissue.

According to another aspect of the invention, an apparatus for cutting or ablating hard tissue, comprises an optical cavity; a gain medium disposed within the optical cavity; a diode light pump disposed within the optical cavity and optically aligned to light pump the gain medium to generate laser light, wherein the generated laser light has a wavelength and power density suitable for cutting and ablating hard tissue.

Additional advantages and aspects of the present invention are apparent in the following detailed description and claims.

DETAILED DESCRIPTION OF THE PRESENT INVENTION

Figure 1A:
FIG. 1a is a schematic illustration of an end-pumped diode laser in accordance with the prior art.

Reference will now be made in detail to particular embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims.

In accordance with one aspect of the present invention, a method of cutting or ablating hard tissue is disclosed, comprising the steps of providing a gain medium, a diode array, and an optical cavity; placing the gain medium and the diode array within the optical cavity so that the diode array is optically aligned to side pump the gain medium; activating the diode array to light pump the gain medium and generate laser light; and directing the laser light onto the hard tissue to cut or ablate the hard tissue.

In accordance with another aspect of the present invention, a method of cutting or ablating hard tissue comprises the steps of providing a gain medium, a diode light pump, and an optical cavity; placing the gain medium and the diode light pump within the optical cavity so that the diode light pump is optically aligned to light pump the gain medium; activating the diode light pump to light pump the gain medium and generate laser light; and directing the laser light onto the hard tissue to cut or ablate the hard tissue.

According to another aspect of the invention, an apparatus for cutting or ablating hard tissues, comprises an optical cavity; a gain medium disposed within the optical cavity; a diode light pump disposed within the optical cavity and optically aligned to light pump the gain medium to generate laser light, wherein the generated laser light has a wavelength and power density suitable for cutting and ablating hard tissue.

In any of the above aspects, the gain medium may comprises a laser rod, such as an Erbium-based laser rod. More particularly, the gain medium may comprises an Erbium-based crystalline laser rod for generating laser light in a range between 1.73 and 2.94 microns. The laser light can be generated in the TEMoo mode to overcome thermal effects. In accordance with a method of the present invention, the hard tissue can comprise, for example, tooth or bone tissue. Temporal pulse control can be used to attain a uniform temporal pulse pattern. In another embodiment, gain switching or Q-switching can be used to attain the uniform temporal pulse pattern. The diode light pump can comprise a diode array, and the diode array can be optically aligned to side pump the gain medium. The diode light pump can be placed within the optical cavity so that the diode array is optically aligned to side pump the gain medium.

Any feature or combination of features described herein are included within the scope of the present invention provided that the features included in any such combination are not mutually inconsistent as will be apparent from the context, this specification, and the knowledge of one of ordinary skill in the art.

The methods and apparatuses of this application are intended for use, to the extent the technology is compatible, with existing technologies including the apparatuses and methods disclosed in any of the following patents and patent applications: U.S. Pat. Nos. 5,741,247; 5,785,521; 5,968,037; 6,086,367; 6,231,567; and U.S. Ser. No. 09/848,010 (filed May 2, 2001), which incorporates by reference the disclosure of U.S. Pat. No. 6,288,499, all of which are assigned to BioLase Technology, Inc. and are incorporated herein by reference. The referenced U.S. Pat. No. 6,288,499 discloses full-width half-max ranges closer to beginnings than ends of pulses and full-width half-max values ranging from about 0.025 to about 250 microseconds.

The diode side pumped Erbium crystalline laser of the present invention may emit at wavelengths between 1.73 and 2.94 µm. The pumping may be accomplished by InGaAs laser diodes configured as bars or arrays emitting at 968 nm, and can be delivered in either a CW (continuous wave) or a QCW (quasi-continuous wave) mode of operation, at power levels that may begin at 40 W. With an optimized output coupling, the light-to-light efficiency can be at least 10% and can reach a magnitude up to 35%. One of the embodiments of this invention is that these efficiency magnitudes are higher than those which may have been previously attained, owing to the inventive design which seeks to maximize the pump-to-laser mode overlap and to optimize outcoupling, specifically tailoring the outcoupling to the pulse format or CW operation of the laser.

The oscillator of the present invention is a plano-plano resonator comprising a high reflectivity mirror and an outcoupling, partially transmitting mirror. For certain applications intracavity elements, such as an electro-optic or acousto-optic cell for Q-switching, or an etalon for wavelength tuning can be introduced. The laser can emit energy in, for example, one of the following modes of operation: CW, gain switched obtained by quasi-CW operation of the pump laser diode, and Q-switched by an acousto-optical (AO) device or Q-switched by an electro-optical (EO) device. Thermal management and temperature control are provided by either air and/or water cooling, with the possibility of using thermo-electric cooling.

In the category of the disclosed diode side pumped lasers included are the following crystals: Er:LiYF$_4$ (Er:YLF) emitting at 1.73 µm on the Er$^{3+4}$I$_{13/2}$⇒$^4$I$_{15/2}$ transition; Er:LiYF$_4$ emitting at 2.80 µm on the Er$^{3+4}$I$_{11/2}$⇒$^4$I$_{13/2}$ transition; Er:Y$_3$Sc$_2$GaSO$_{12}$ (Er:YSGG) emitting at 2.79 µm on the Er$^{3+4}$I$_{11/2}$⇒$^4$I$_{13/2}$ transition; Er:Gd$_3$Sc$_2$GaSO$_{12}$ (Er:GSGG) emitting at 2.8 µm on the Er$^{3+4}$I$_{11/2}$⇒$^4$I$_{13/2}$ transition; Er:Gd$_3$GaSO$_{12}$ (Er:GGG) emitting at 2.82 µm on the Er$^{3+4}$I$_{11/2}$⇒$^4$I$_{13/2}$ transition; Er,Tm:Y$_3$Al$_5$O$_{12}$ (TE:YAG) emitting at 2.69 µm on the Er$^{3+4}$I$_{11/2}$⇒$^4$I$_{13/2}$ transition; Er:KYF$_4$ emitting at 2.81 µm on the Er$^{3+4}$I$_{11/2}$⇒$^4$I$_{13/2}$ transition; Ho,Yb:KYF$_4$ emitting at 2.84 µm on the Ho$^{3+5}$I$_6$⇒$^5$I$_7$ transition; Er:Y$_3$Al$_5$O$_{12}$ (Er:YAG) emitting at 2.94 µm on the Er$^{3+4}$I$_{11/2}$⇒$^4$I$_{13/2}$ transition; Er:Y$_3$AlO$_3$ (Er:YALO) emitting at 2.71 µm on the Er$^{3+4}$I$_{11/2}$⇒$^4$I$_{13/2}$ transition; Er:KGd (WO$_4$)$_s$ (Er:KGW) emitting at 2.8 µm on the Er$^{3+4}$I$_{11/2}$⇒$^4$I$_{13/2}$ transition; Er:KY(WO$_4$)$_s$ (Er:KYW); Er:Al$_3$O$_3$ emitting on the Er$^{3+4}$I$_{11/2}$⇒$^4$I$_{13/2}$ transition; Er:Lu$_2$O$_3$ emitting at emitting at 2.7 µm on the Er$^{3+4}$I$_{11/2}$⇒$^4$I$_{13/2}$ transition; Er:CaF$_2$ emitting at 2.75-2.85 µm on the Er$^{3+4}$I$_{11/2}$⇒$^4$I$_{13/2}$ transition; Cr,Tm,Er:Y$_3$Al$_5$O$_{12}$ (CTE:YAG) emitting at 2.7 µm on the Er$^{3+4}$I$_{11/2}$⇒$^4$I$_{13/2}$ transition; Er:BaLu$_2$F$_8$ emitting at 2.8 µm on the Er$^{3+4}$I$_{11/2}$⇒$^4$I$_{13/2}$ transition; Er:BaY$_2$F$_8$ (Er:BYF) emitting at 2.7 µm on the Er$^{3+4}$I$_{11/2}$⇒$^4$I$_{13/2}$ transition; and Cr:ZnSe emitting at 2-3 µm.

Due to their efficient interaction with biological tissue and water, these lasers are useful as surgical instruments, in the areas of, for example, dental surgery, orthopedic surgery, tissue ablation, bone cutting and soft tissue surfacing. Particular application may include use of the laser for expansion of atomized water or fluid particles above a target surface for mechanical cutting or ablation, such as disclosed in U.S. Pat. No. 5,741,247, entitled Atomized Fluid Particles for Electromagnetically Induced Cutting, and U.S. Pat. No. 5,785,521, entitled Fluid Conditioning System, the contents of which are expressly incorporated herein by reference.

Another embodiment of the side diode pumped erbium lasers and Ho,Yb:KYF4 laser is that when operated in pulses, the pulsed format is highly repetitive in time and intensity. This performance can facilitate precise and predictable cutting, and can improve cutting efficiency. In dental and medical applications, this feature is consistent with less heat or thermal denaturation of the tissue, which can provide for quicker healing.

Figure 2A:
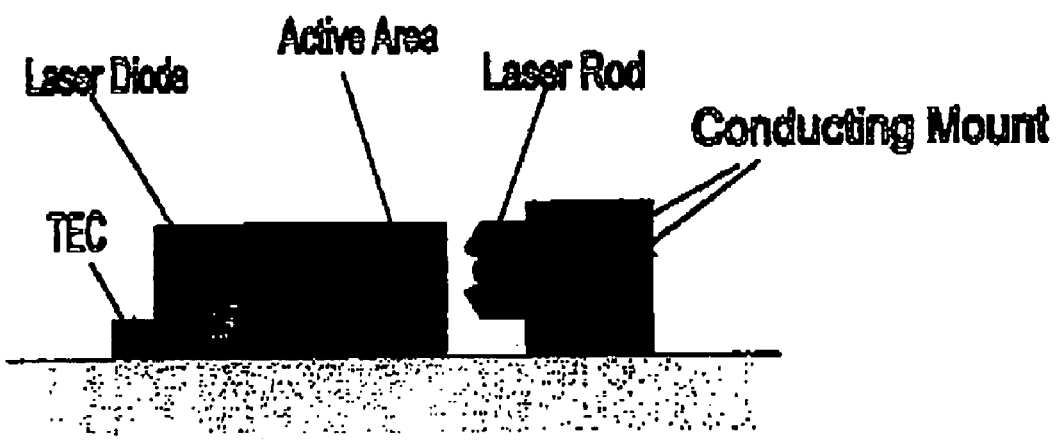
FIG. 2a is a schematic top view of a laser head according to the present invention.
Figure 2B:
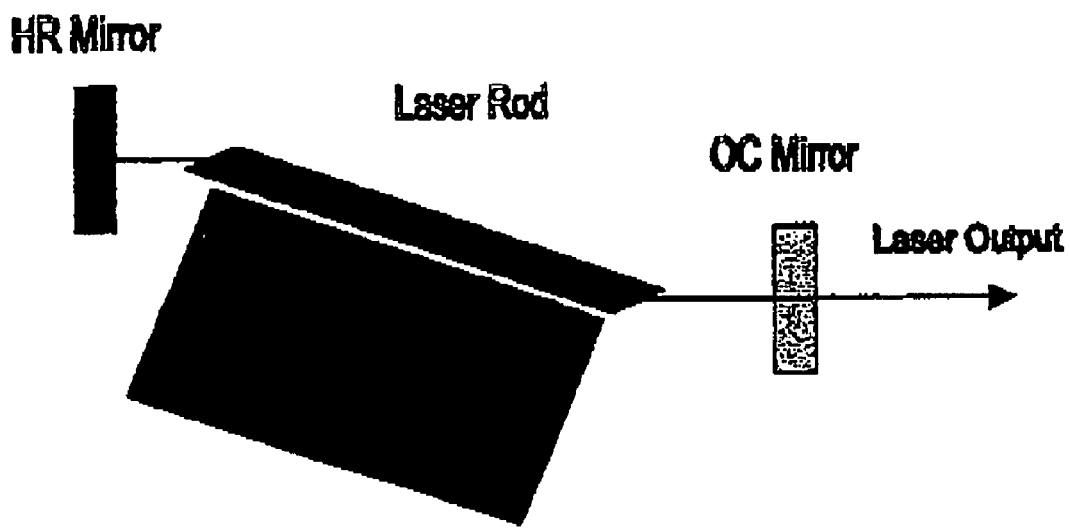
FIG. 2b is a schematic side view of a laser head according the the present invention.

The present invention is configured as shown in FIGS. 1a, 2a and 2b. It applies the side-pumped configuration to: 1) pumping of erbium and Ho,Yb:KYF4 crystals to extract laser emission in the 1.73 and 2.94 µm range, 2) dental and medical cutting and resurfacing by mainly the 2.69 to 2.95 µm range, 3) optimization of the dental and medical process by efficient delivery of the laser to the target and minimal thermal process. Configuration of the crystal itself can be rectangular or round. A rectangular shape may be preferred in one embodiment, although a cylindrical shape may function well in modified embodiments. The pumping wavelength should be chosen to be efficiently transferred into the crystal, wherein for example the radiation wavelength of the diode pumping source matches a peak absorption of the active media or crystal. In one embodiment a lens may be used to couple the pump source to the laser rod. Cooling sources and/or lenses may be positioned between the pump source and the laser rod. Regarding FIGS. 2a and 2b, FIG. 2a is a schematic top view of a laser head according to the present invention wherein "TEC" denotes thermo electric cooler, and FIG. 2b is a schematic side view of a laser head according to the present invention wherein opposing ends of the laser rod are cut to the Brewster angle to provide polarization.

Figure 3:
FIG. 3 is a regulated laser pulse format according to the present invention.

Regarding the present invention's application of the side-pumped configuration to optimize dental and medical processes by efficient delivery of the laser to the target and minimal thermal process, optimization is accomplished by radiating the target with a train of well regulated pulses, as shown in FIG. 3. What is shown is a sequence of narrow pulses, each having a sufficiently high power, for instance 20 kW, and an energy of 8 mJ. With a duty cycle of 0.02% this determines an average power of 4 W. A number of methods may be employed to attain such a pulse format, among them: gain switching and Q-switching by either an electro-optical or an acousto-optical Q-switch.

Figure 4C:
FIG. 4c shows the resulting laser pulse from FIGS. 4a and 4b according to the present invention.
Figure 1B:
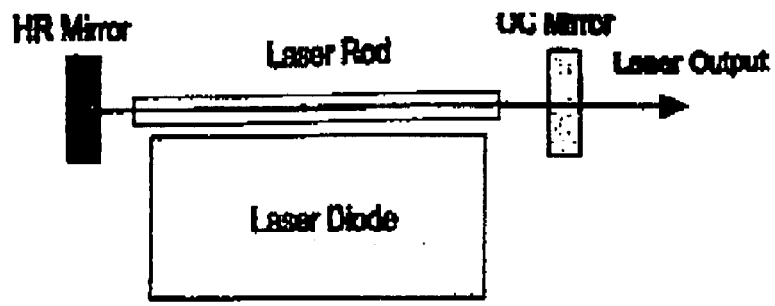
FIG. 1b is a side-pumped diode laser according to the present invention.
Figure 4A:
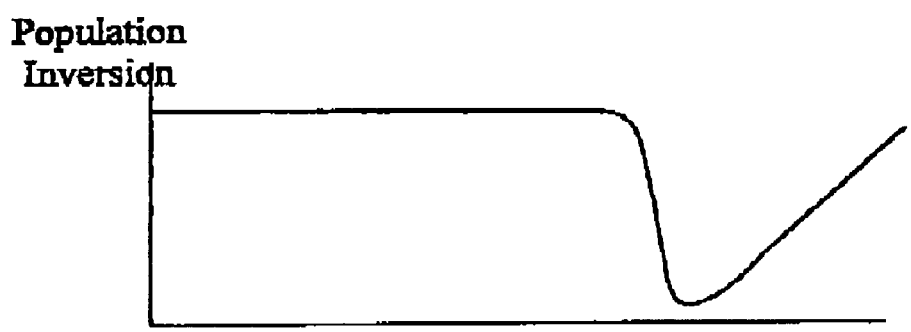
FIG. 4a shows the population inversion in a CW pumping regime according to the present invention.
Figure 4B:
FIG. 4b shows the resonator Q due to the Q-switch hold-off according to the present invention.

The Q-switch temporal trace is shown in FIGS. 4a-4c, wherein FIG. 4a shows the population inversion in a CW pumping regime, FIG. 4b shows the resonator Q due to the Q-switch hold-off, and FIG. 4c corresponds generally to FIG. 3 and shows the resulting laser pulse.

Figure 5A:
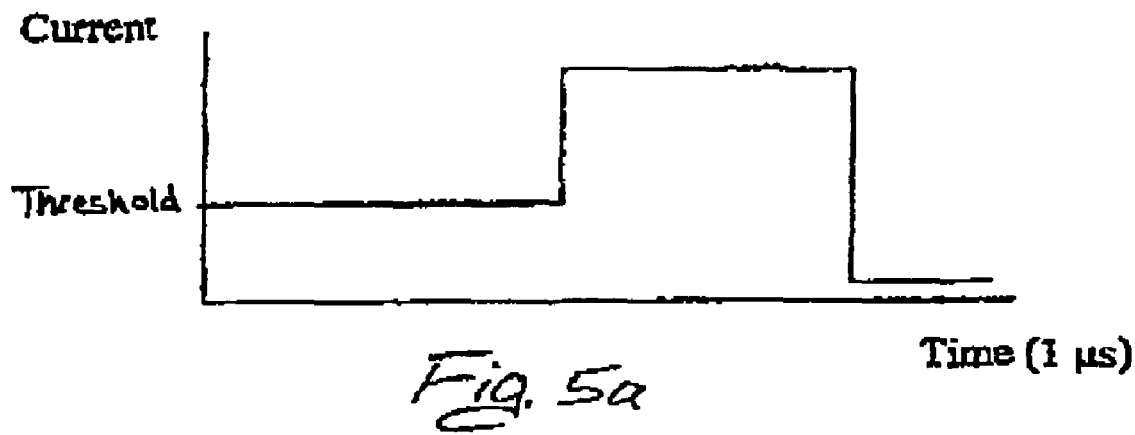
FIG. 5a shows the quasi CW current supplied to the pumping laser diode according to the present invention.
Figure 5B:
FIG. 5b shows the population inversion in the quasi CW pumping according to the present invention.
Figure 5C:
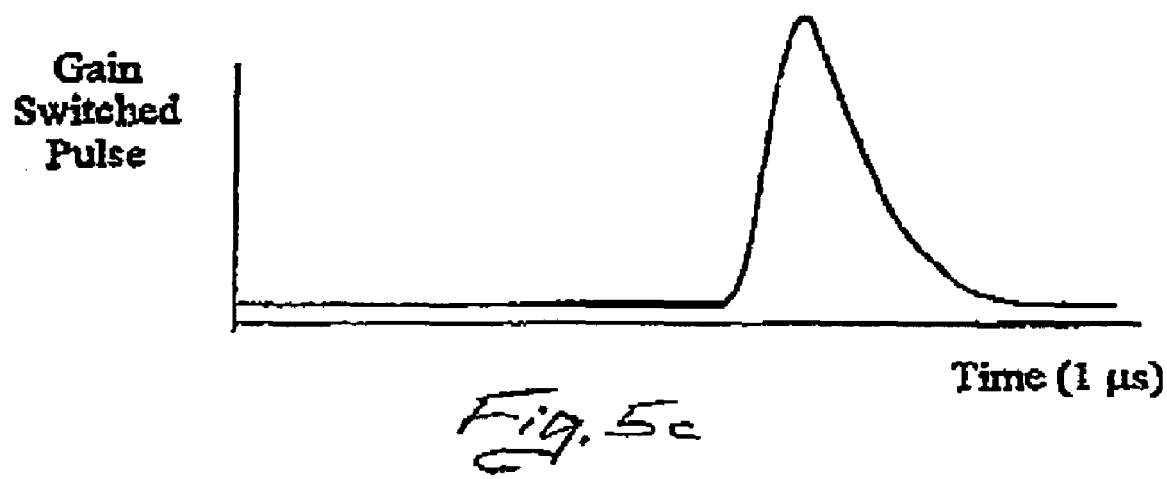
FIG. 5c shows resulting laser pulse from FIGS. 5a and 5b according to the present invention.
Figure 6:
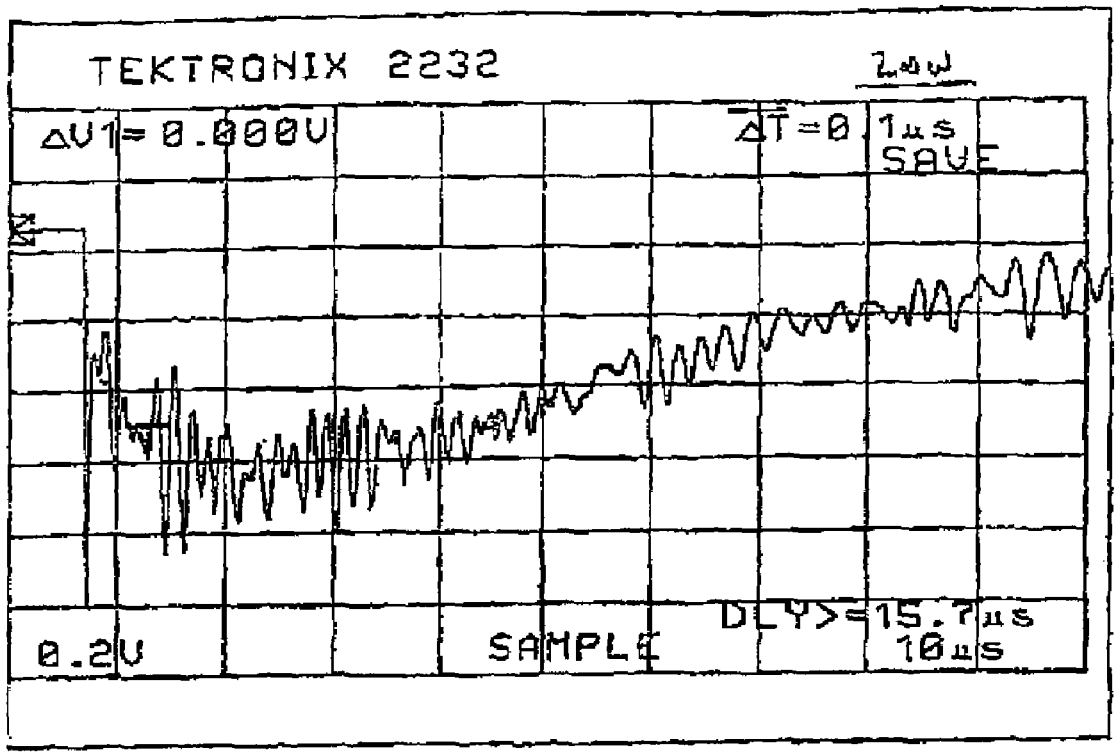
FIG. 6 is a representation corresponding to a preferred pulse shape.
Figure 7:
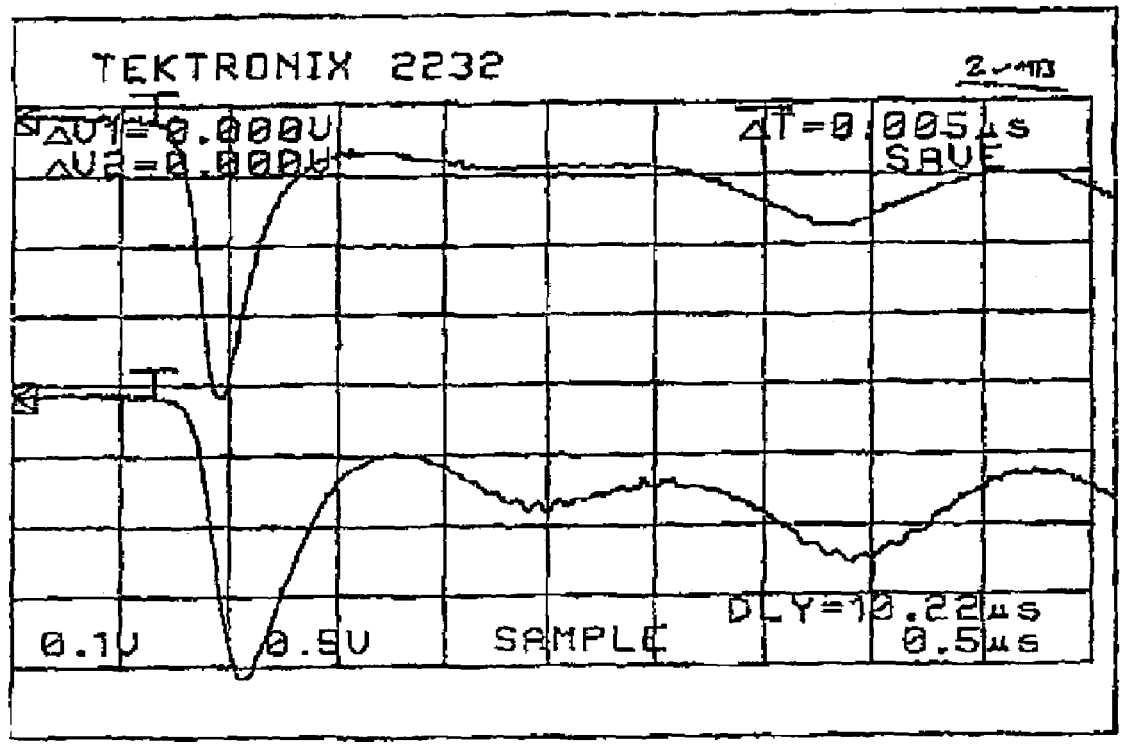
FIG. 7 is a close-up view of a pulse of FIG. 6.

The gain switch temporal trace is shown in FIGS. 5a-5c, wherein FIG. 5a shows the quasi-CW (QCW) current supplied to the pumping laser diode, FIG. 5b shows the population inversion in the QCW pumping regime, and FIG. 5c shows the resulting laser pulse. Because in gain switching the resonator Q is never spoiled, the pulse evolves simultaneously with the buildup of the population inversion. Hence, the dynamics are similar to a free running laser, as in the pulse train shown in FIG. 6. However, as shown in FIG. 5a, the gain is dropped to below threshold once the first spike is generated, thus a gain switch pulse is formed as the first spike only, as shown in FIG. 7. Additional description is provided in the following table.

| parameter | Range | Embodiment | Example |
| --- | --- | --- | --- |
| Wavelength | 1.5-6.0 μm | 2.6-3.0 μm | 2.78 μm |
| Pulse duration | 0.1-1000 μsec | 0.1-5.0 μsec | 1 μsec |
| Pulse repetition rate | 1-1000 Hz (or in envelopes of 5-20 pulses separated by 1.0-10 μsec) | 1-200 Hz | 100 Hz |
| Energy per pulse | 3-1000 mJ | 10-500 mJ | 50-100 mJ |
| Average power | 0.1-100 W | 0.1-10 W | 8 W |
| Spot size | 20-5000 μm | 50-1000 μm | 500 μm |

As mentioned above, particular applications of the current invention may include use of the laser for expansion of atomized water or fluid particles above a target surface for mechanical cutting or ablation. The above-referenced U.S. Pat. No. 6,288,499 discloses (a) output optical energy distributions including output pulses of optical (e.g., laser) energy having full-width half-max ranges closer to beginnings than ends of the output pulses and (b) full-width half-max values of the output pulses ranging from about 0.025 to about 250 microseconds.

Figure 8:
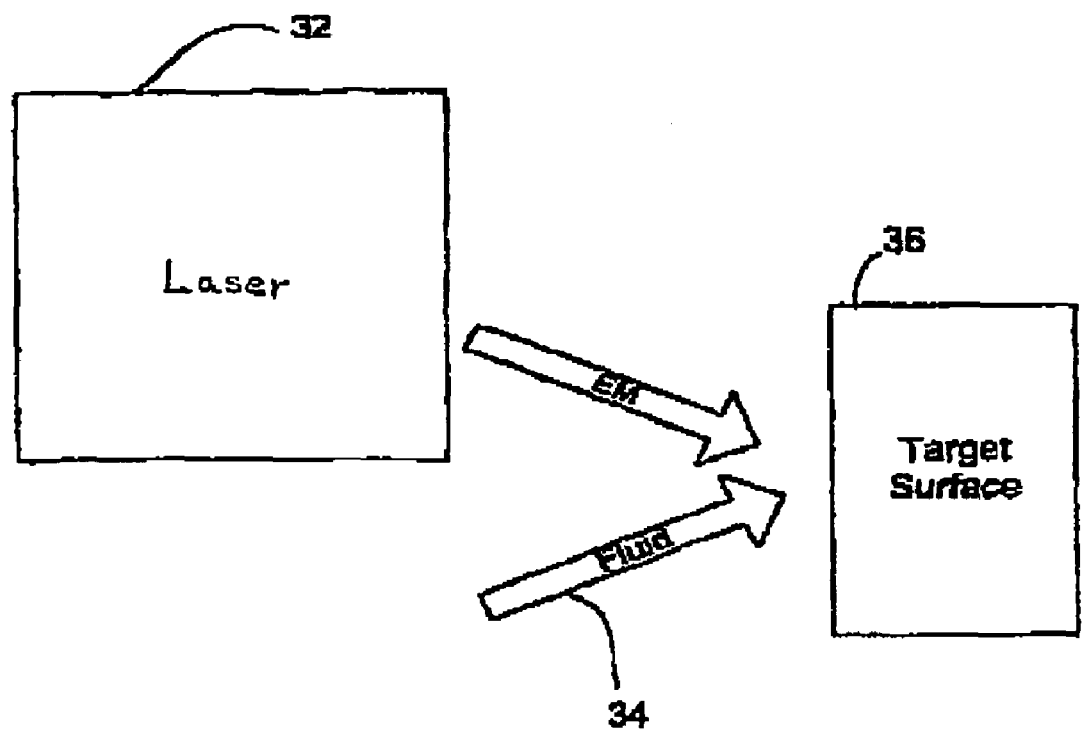
FIG. 8 is a block diagram showing a fluid used in combination with a laser in accordance with an embodiment of the present invention.

With reference to FIG. 8, output pulses of output optical energy distributions can be useful for maximizing a cutting effect of an electromagnetic energy source 32, such as a laser driven by a diode or flashlamp driving circuit 30, directed into a distribution (e.g., an atomized distribution) of fluid particles 34 above a target surface 36. An apparatus for directing output pulses of electromagnetic energy into a distribution of fluid particles above a target surface is disclosed in the mentioned U.S. Pat. No.5,741,247. High-intensity leading micropulses 64, 66, and 68 (FIG. 9, infra) of the output pulse can be used to impact large amounts of energy into fluid particles to thereby expand the fluid particles and apply mechanical cutting forces to the target surface. The trailing micropulses after the maximum micropulse 68 have been found to further enhance the cutting efficiency. According to an aspect of the present invention, a single large leading micropulse 68 may be generated or, alternatively, two or more large leading micropulses 68 (or 64, 66, for example) may be generated.

Figure 9:
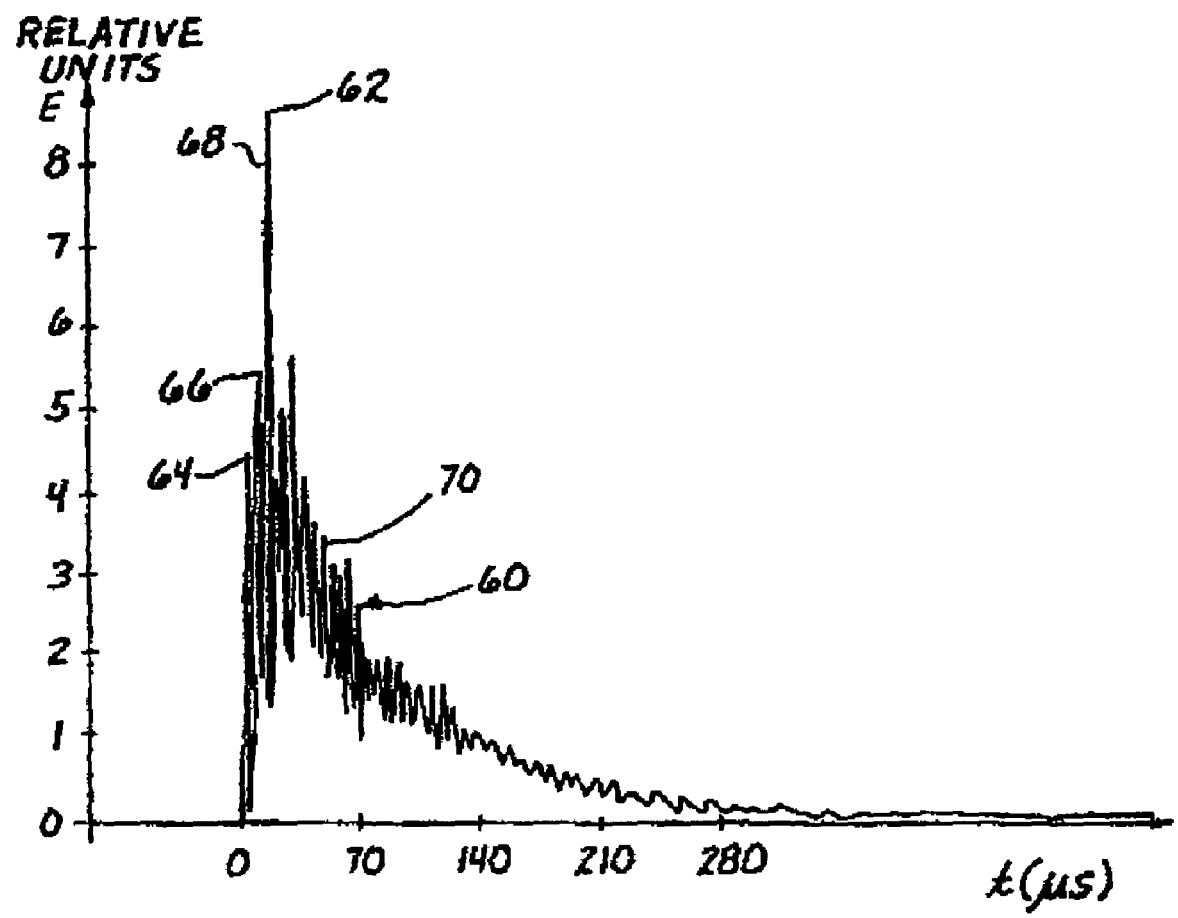
FIG. 9 is a plot of output optical energy versus time for a laser system in accordance with an aspect of the present invention.

With reference to FIG. 9, an output optical energy distribution over time of an electromagnetic energy source according to an aspect of the present invention is illustrated at 60. In the illustrated embodiment, the pulse width is about 200 microseconds. The output optical energy distribution 60 comprises a maximum value 62, a number of leading micropulses 64, 66, 68, and a portion of generally declining optical energy 70. As illustrated in FIG. 9, the micropulse 68 comprises a maximum value 62 which is at or near the very beginning of the output pulse. Additionally, the full-width half-max values of the output optical energy distribution (e.g., output pulse) in FIG. 9 is approximately 70 microseconds. Applicants' invention contemplates output pulses comprising full-width half-max values greater than 0.025 microseconds. In some embodiments, the full-width half-max values range from about 0.25 microseconds to about 250 micorseconds and, more preferably, range from 10 to 150 microseconds, but other ranges may also be possible. Additionally, Applicants' invention contemplates an output pulse width of between 0.25 and 300 microseconds, for example.

As used herein, the full-width half-max range is defined from a beginning time, where the amplitude first rises above one-half the peak amplitude, to an ending time, wherein the amplitude falls below one-half the peak amplitude a final time during the pulse width. The full-width half-max value is defined as the difference between the beginning time and the ending time. The location of the full-width half-max range along the time axis, relative to the output pulse width, is closer to the beginning of the pulse than the end of the pulse. The location of the full-width half-max range is preferably within the first half of the pulse and, more preferably, is within about the first third of the output pulse along the time axis. Other locations of the full-width half-max range are also possible in accordance with the present invention. The beginning time of the full-width half-max range preferably occurs within the first 10 to 15 microseconds and, more preferably, occurs within the first 12.5 microseconds from the leading edge of the output pulse. The beginning time, however, may occur either earlier or later within the output pulse. The beginning time is preferably achieved within the first tenth of the pulse width.

In view of the foregoing, it will be understood by those skilled in the art that the methods of the present invention can facilitate formation of laser devices, and in particular side-pumped diode laser systems. The above-described embodiments have been provided by way of example, and the present invention is not limited to these examples. Multiple variations and modification to the disclosed embodiments will occur, to the extent not mutually exclusive, to those skilled in the art upon consideration of the foregoing description. Such variations and modifications, however, fall well within the scope of the present invention as set forth in the following claims.

What is claimed is:

1. A method of cutting or ablating hard tissue, comprising the following steps:
   providing a gain medium, a diode array, and an optical cavity;
   placing the gain medium and the diode array within the optical cavity so that the diode array is optically aligned to side pump the gain medium;
   activating the diode array to light pump the gain medium and generate at least one pulse of laser light having a full-width half-max range closer to a beginning than an end of the pulse, the laser light having a wavelength, pulse format, and power density suitable for cutting and ablating hard tissue and further having a wavelength which is highly absorbed by water;
   placing fluid into a volume in close proximity to the hard tissue; and
   directing pulses of the laser light into the volume in close proximity to the hard tissue to cause laser light to be highly absorbed by fluid in the volume and to effectuate the cutting or ablating of the hard tissue.

2. The method as set forth in claim 1, wherein the gain medium comprises a laser rod.

3. The method as set forth in clam 1, wherein the gain medium comprises an Erbium-based laser rod.

4. The method as set forth in claim 1, wherein the laser light is generated in the TEMoo mode to overcome thermal effects.

5. The method as set forth in claim 1, wherein the hard tissue comprises tooth tissue.

6. The method as set forth in claim 1, wherein the hard tissue comprises bone.

7. The method as set forth in claim 1, wherein temporal pulse control is used to attain a uniform temporal pulse pattern.

8. The method as set forth in claim 7, wherein gain switching or Q-switching is used in attaining the uniform temporal pulse pattern.

9. The method as set forth in claim 1, wherein the laser light has a wavelength in a range from about 2.69 μm to about 2.95 μm.

10. A method of cutting or ablating hard tissue, comprising the following steps:
    providing a gain medium, a diode light pump, and an optical cavity;
    placing the gain medium and the diode light pump within the optical cavity so that the diode light pump is optically aligned to light pump the gain medium;
    activating the diode light pump to light pump the gain medium and generate at least one pulse of laser light having a full-width half-max value in a range from about 0.025 to about 250 microseconds, the laser light having a pulse format and a wavelength which are suitable for cutting and ablating hard tissue and which are highly absorbed by water;
    placing fluid into a volume in close proximity to the hard tissue; and
    directing pulses of the laser light into the volume in close proximity to the hard tissue to cause laser light to be highly absorbed by fluid in the volume and to generate the cutting or ablating of the hard tissue.

11. The method as set forth in claim 10, wherein the gain medium comprises a laser rod.

12. The method as set forth in claim 10, wherein the gain medium comprises an Erbium-based laser rod.

13. The method as set forth in claim 10, wherein the laser light is generated in the TEMoo mode to overcome thermal effects.

14. The method as set forth in claim 10, wherein the hard tissue comprises tooth tissue.

15. The method as set forth in claim 10, wherein the hard tissue comprises bone.

16. The method as set forth in claim 10, wherein temporal pulse control is used to attain a uniform temporal pulse pattern.

17. The method as set forth in claim 16, wherein gain switching or Q-switching is used in attaining the uniform temporal pulse pattern.

18. The method as set forth in claim 10, wherein the diode light pump comprises a diode array.

19. The method as set forth in claim 10, wherein the diode light pump comprises a diode array, which is placed within the optical cavity so that the diode array is optically aligned to side pump to gain medium.

20. The method as set forth in claim 10, wherein the laser light has a wavelength in a range from about 2.69 μm to about 2.95 μm.

21. An apparatus for cutting or ablating hard tissue, comprising:
    an optical cavity;
    a gain medium disposed within the optical cavity;
    a fluid output configured to place fluid into a volume in close proximity to the hard tissue; and
    a diode light pump disposed within the optical cavity and optically aligned to light pump the gain medium to generate at least one pulse of laser light having a full-width half-max range closer to a beginning than an end of the pulse, wherein the generated laser light has a wavelength, pulse, and power density suitable for cutting and ablating hard tissue and further has a wavelength that is highly absorbed by water, the apparatus being configured to direct the laser light into the volume in close proximity to the hard tissue to cause laser light to be highly absorbed by fluid in the volume whereby the hard tissue is cut or ablated, wherein the laser light is generated in the TEMoo mode to overcome thermal effects.

22. The apparatus as set forth in claim 21, wherein the gain medium comprises a laser rod.

23. The apparatus as set forth in claim 21, wherein the gain medium comprises an Erbium-based laser rod.

24. An apparatus for cutting or ablating hard tissue, comprising:
    an optical cavity;
    a gain medium disposed within the optical cavity;
    a fluid output configured to place fluid into a volume in close proximity to the hard tissue; and
    a diode light pump disposed within the optical cavity and optically aligned to light pump the gain medium to generate at least one pulse of laser light having a full-width half-max range closer to a beginning than an end of the pulse, wherein the generated laser light has a wavelength, pulse, and power density suitable for cutting and ablating hard tissue and further has a wavelength that is highly absorbed by water, the apparatus being configured to direct the laser light into the volume in close proximity to the hard tissue to cause laser light to be highly absorbed by fluid in the volume whereby the hard tissue is cut or ablated, wherein the generated laser light has a wavelength, pulse, and power density suitable for cutting and ablating tooth tissue.

25. An apparatus for cutting or ablating hard tissue, comprising:

an optical cavity;

a gain medium disposed within the optical cavity;

a fluid output configured to place fluid into a volume in close proximity to the hard tissue; and a diode light pump disposed within the optical cavity and optically aligned to light pump the gain medium to generate at least one pulse of laser light having a full-width half-max range closer to a beginning than an end of the pulse, wherein the generated laser light has a wavelength, pulse, and power density suitable for cutting and ablating hard tissue and further has a wavelength that is highly absorbed by water, the apparatus being configured to direct the laser light into the volume in close proximity to the hard tissue to cause laser light to be highly absorbed by fluid in the volume whereby the hard tissue is cut or ablated, wherein the generated laser light has a wavelength, pulse, and power density suitable for cutting and ablating bone.

26. An apparatus for cutting or ablating hard tissue, comprising:

an optical cavity;

a gain medium disposed within the optical cavity;

a fluid output configured to place fluid into a volume in close proximity to the hard tissue; and a diode light pump disposed within the optical cavity and optically aligned to light pump the gain medium to generate at least one pulse of laser light having a full-width half-max range closer to a beginning than an end of the pulse, wherein the generated laser light has a wavelength, pulse, and power density suitable for cutting and ablating hard tissue and further has a wavelength that is highly absorbed by water, the apparatus being configured to direct the laser light into the volume in close proximity to the hard tissue to cause laser light to be highly absorbed by fluid in the volume whereby the hard tissue is cut or ablated, wherein temporal pulse control is used to attain a uniform temporal pulse pattern.

27. The apparatus as set forth in claim 26, wherein gain switching or Q-switching is used in attaining the uniform temporal pulse pattern.

28. An apparatus for cutting or ablating hard tissue, comprising:

an optical cavity;

a gain medium disposed within the optical cavity;

a fluid output configured to place fluid into a volume in close proximity to the hard tissue; and a diode light pump disposed within the optical cavity and optically aligned to light pump the gain medium to generate at least one pulse of laser light having a full-width half-max range closer to a beginning than an end of the pulse, wherein the generated laser light has a wavelength, pulse, and power density suitable for cutting and ablating hard tissue and further has a wavelength that is highly absorbed by water, the apparatus being configured to direct the laser light into the volume in close proximity to the hard tissue to cause laser light to be highly absorbed by fluid in the volume whereby the hard tissue is cut or ablated, wherein the diode light pump comprises a diode array.

29. The apparatus as set forth in claim 28, wherein the diode array is optically aligned to side pump the gain medium.

30. The apparatus as set forth in claim 29, wherein the gain medium comprises a laser rod.

31. The apparatus as set forth in claim 30, wherein the gain medium comprises an Erbium-based laser rod.

32. The apparatus as set forth in claim 29, wherein the gain medium comprises an Erbium-based crystalline laser rod for generating laser light in a range between 1.73 and 2.94 microns.

33. The apparatus as set forth in claim 29, wherein the laser light is generated in the TEMoo mode to overcome thermal effects.

34. The apparatus as set forth in claim 29, wherein the generated laser light has a wavelength, pulse, and power density suitable for cutting and ablating tooth tissue.

35. The apparatus as set forth in claim 29, wherein the generated laser light has a wavelength, pulse, and power density suitable for cutting and ablating bone.

36. The apparatus as set forth in claim 29, wherein temporal pulse control is used to attain a uniform temporal pulse pattern.

37. The apparatus as set forth in claim 36, wherein gain switching or Q-switching is used in attaining the uniform temporal pulse pattern.

38. The method as set forth in claim 28, wherein the laser light has a wavelength in a range from about 2.69 µm to about 2.95 µm.

* * * * *